United States Patent
Horn et al.

(10) Patent No.: US 11,407,935 B2
(45) Date of Patent: Aug. 9, 2022

(54) HEAT-SENSITIVE RECORDING MATERIAL

(71) Applicant: PAPIERFABRIK AUGUST KOEHLER SE, Oberkirch (DE)

(72) Inventors: Michael Horn, Offenburg (DE); Timo Stalling, Appenweier (DE)

(73) Assignee: PAPIERFABRIK AUGUST KOEHLER SE, Oberkirch (DE)

( * ) Notice: Subject to any disclaimer, the term of this patent is extended or adjusted under 35 U.S.C. 154(b) by 0 days.

(21) Appl. No.: 17/417,002

(22) PCT Filed: Dec. 19, 2019

(86) PCT No.: PCT/EP2019/086224
§ 371 (c)(1),
(2) Date: Jun. 21, 2021

(87) PCT Pub. No.: WO2020/127675
PCT Pub. Date: Jun. 25, 2020

(65) Prior Publication Data
US 2022/0041923 A1 Feb. 10, 2022

(30) Foreign Application Priority Data
Dec. 20, 2018 (DE) ...................... 10 2018 133 168.1

(51) Int. Cl.
| | | |
|---|---|---|
| *C09K 9/02* | (2006.01) | |
| *C07C 317/42* | (2006.01) | |
| *B41M 5/327* | (2006.01) | |
| *B41M 5/333* | (2006.01) | |

(52) U.S. Cl.
CPC ............. *C09K 9/02* (2013.01); *B41M 5/3275* (2013.01); *B41M 5/3333* (2013.01); *C07C 317/42* (2013.01); *C09K 2211/1007* (2013.01)

(58) Field of Classification Search
CPC . C09K 9/02; C09K 2211/1007; C07C 317/42; B41M 5/3275; B41M 5/3333
See application file for complete search history.

(56) References Cited

U.S. PATENT DOCUMENTS

| | | | |
|---|---|---|---|
| 2009/0082202 A1 | 3/2009 | Stork et al. | |
| 2015/0284321 A1* | 10/2015 | Sakai | B41M 5/3336 |
| | | | 428/195.1 |
| 2017/0190199 A1* | 7/2017 | Horn | B41M 5/3333 |
| 2018/0079243 A1* | 3/2018 | Horn | B41M 5/3333 |
| 2020/0172477 A1 | 6/2020 | Horn et al. | |

FOREIGN PATENT DOCUMENTS

| | | | | |
|---|---|---|---|---|
| CN | 104797429 A | 7/2015 | | |
| DE | 102006032523 A1 | 7/2006 | | |
| DE | 102014107567 B3 | 5/2014 | | |
| DE | 102017111439 A1 | 5/2017 | | |
| DE | 102017122800 A1 | 9/2017 | | |
| EP | 0526072 A1 | 7/1992 | | |
| EP | 0620122 B1 | 3/1996 | | |
| EP | 2033799 A1 | 3/2009 | | |
| EP | 2332529 A1 * | 6/2011 | ........... | A61K 31/136 |
| EP | 2923851 A1 | 9/2015 | | |
| JP | 532061 A | 2/1993 | | |
| JP | H11268421 A | 10/1999 | | |
| WO | 200035679 | 6/2000 | | |
| WO | 2014080615 A1 | 5/2014 | | |
| WO | 2018015178 A1 | 1/2018 | | |
| WO | 2018145874 A1 | 8/2018 | | |
| WO | 2018215287 A1 | 11/2018 | | |

OTHER PUBLICATIONS

Office Action for Korean Application No. 10-2021-7022252, dated Sep. 1, 2021, 3 pages.
Office Action for German Patent Application No. 102018133168.1, dated Nov. 21, 2019, 10 pages.
International Search Report and Written Decision for Application No. PCT/EP2019/086224, dated Apr. 6, 2020, 13 pages.
Office Action for Japanese Application No. 2021535227, dated Nov. 26, 2021, 4 pages.
Office Action for Chinese Application No. 201980082885.5, dated Dec. 7, 2021, 6 pages.
Office Action for Korean Application No. 10-2021-70222252, dated Nov. 3, 2021, 4 pages.

\* cited by examiner

*Primary Examiner* — Bijan Ahvazi
(74) *Attorney, Agent, or Firm* — Fay Sharpe LLP

(57) ABSTRACT

Described are colour developers of formula (I) $Ar^1$—$SO_2$—NH—$C_6H_4$—$SO_2$—$C_6H_4$—NH—CO—NH—$Ar^2$ (I), a heat-sensitive recording material, comprising a carrier substrate and also a heat-sensitive, colour-forming layer comprising at least one colour former and at least one phenol-free colour developer, the at least one colour developer being the compound of formula (I), and a method for producing this heat-sensitive recording material.

17 Claims, No Drawings

HEAT-SENSITIVE RECORDING MATERIAL

The invention relates to a colour developer, a heat-sensitive recording material, comprising a carrier substrate and also a heat-sensitive, colour-forming layer comprising at least one colour former and at feast one phenol-free colour developer, a method for producing this heat-sensitive recording material, and the use of the heat-sensitive recording material.

Heat-sensitive recording materials (thermal papers) for direct thermal printing applications which have a heat-sensitive colour-forming layer (thermal reaction layer) applied to a carrier substrate have been known for a long time. The heat-sensitive colour-forming layer usually contains a colour former and a colour developer, which react with each other under the influence of heat and thus lead to colour development. Inexpensive (bis)phenolic colour developers, such as bisphenol A and bisphenol S, are widely used to obtain heat-sensitive recording materials with an acceptable performance profile for numerous applications. Also known are heat-sensitive recording materials that, contain a non-phenolic colour-developer in the heat-sensitive colour-forming layer. These have been developed to improve the resistance of the typeface, especially if the printed heat-sensitive recording material is to be stored for longer periods of time at higher temperatures and/or humidity. Especially against the background of the public discussions regarding the toxic potential of (bis)phenolic chemicals, interest in non-phenolic colour developers has risen sharply. The aim here was to avoid the disadvantages of (bis)phenolic colour developers, but to at least maintain, and preferably improve, the technical performance properties that can be achieved with phenolic colour developers.

The prior art on non-phenolic colour developers reveals common structural characteristics despite the great chemical diversity of these substances.

For example, a 1,3-disubstituted (thio)ureido substructure (Y—NH—C(X)—NH—Z with X=S or O) is a common feature of numerous non-phenolic colour developers. The functional properties relevant for suitability as a colour developer can be modulated by appropriate selection of the Y and Z groups.

Colour developers with sulfonylurea structures (—$SO_2$—NH—CO—NH—) are widely used because they are relatively easy to produce and the heat-sensitive recording materials they produce have good application properties.

EP 0 526 072 A1 and EP 0 620 122 B1 disclose colour developers from the class of aromatic sulfonyl(thio)ureas. With these, heat-sensitive recording materials can be obtained that are characterised by a relatively high image resistance. Furthermore, the heat-sensitive recording materials based on these colour developers have a useful thermal sensitivity with good surface whiteness, so that, if the formulation of the heat-sensitive colour-forming layer is appropriately designed, it is comparatively easy to produce high print densities using commercially available thermal printers.

WO 0 035 679 A1 discloses aromatic and heteroaromatic sulfonyl(thio)urea compounds (X=S or O) and/or sulfonyl guanidines (X=NH) of the formula $Ar^1$—$SO_2$—NH—C(X)—NH—Ar, wherein Ar is linked to other aromatic groups by a divalent linker group. A non-phenolic colour developer from this class, 4-methyl-N-(((3-(((4-methylphenyl)sulfonyl)oxy)phenyl)amino]carbonyl)benzenesulfonamide (trade name Pergafast 201®, BASF), which is widely used in practice, is characterised by the balance of the application properties of the heat-sensitive recording materials produced with this colour developer. Especially, these materials have good dynamic responsiveness and, compared to recording materials obtained with (bis)phenolic colour developers, higher resistance of the print when stored under harsh environmental conditions or with respect to hydrophobic substances.

Sulfonylureas tend towards hydrolytic decomposition reactions in the presence of water/moisture and/or heat (M. Eckhardt, T. J. Simat, Chemosphere, 186, 1016 (2017)). As a result, heat-sensitive recording materials may experience partial decomposition of the colour developer when stored in the unprinted state under conditions of elevated humidity and/or temperature.

Since the writing performance (dynamic responsiveness) of heat-sensitive recording materials also depends on the amount of colour developer present in the heat-sensitive layer, a heat-sensitive recording material stored for longer periods of time loses part of the colour developer and thus partially loses its writing performance.

The above-mentioned possibility of modulating the properties of the 1,3-disubstituted (thio)ureido sub-structure can also be achieved by including structural units that are favourably conjugated to the ureido unit.

Such an approach was adopted for example in EP 2 923 851 A1. For example, EP 2 923 851 A1 discloses colour developers of the general formula $R^1$—NH—CO—NH—Ar—NH—$SO_2$—$R^2$, wherein $R^1$, $R^2$ and Ar may be (un)substituted aryl groups.

Although a good dynamic sensitivity can be ensured with the heat-sensitive recording materials based on these colour developers, the stability of the colour complex—especially in relation to plasticisers or adhesives—requires improvement.

The aim of the present invention is to overcome the disadvantages of the prior art described above. Especially, the aim of the present invention lies in providing a colour developer and a heat-sensitive recording material containing same, which recording material has a balanced application property profile and achieves a print density suitable for practical use, comparable to that of known non-phenolic colour developer agents, but at the same time ensures a high resistance of the printed image, especially when the heat-sensitive layer is contacted with hydrophobic substances, such as plasticisers from film materials, oils, fats, and the like, preferably without having to rely on special formulation components in the heat-sensitive function layer, such as antioxidants or special melting aids with limited availability and/or high price. A further aim of the present invention is to provide a colour developer or a heat-sensitive recording material which is able to ensure the functional properties required for application (especially the thermal responsiveness), even when the unprinted heat-sensitive recording material is stored for longer periods of time and/or under extreme climatic conditions (high humidity and/or temperature).

In accordance with the invention these aims are addressed by the use of a compound according to claim 1 in a heat-sensitive recording material according to claim 10.

It has surprisingly been found that it is possible, using colour developers of the specific substitution pattern of formula (I) below, to obtain heat-sensitive recording materials that are characterised by excellent resistance of the typeface, especially even if the printed image is exposed to hydrophobic substances such as plasticisers. The recording materials produced with the colour developers according to the invention also have excellent long-term storage stability. The optical density achieved with printing in thermal printers thus hardly suffers, not even after storage in the unprinted state over several weeks with high ambient humidity and/or at high temperatures. Lastly, the temperature from which the white heat-sensitive recording material produced with the colour developers according to the invention greys noticeably is significantly higher than for heat-sensitive recording materials with known colour developers; in other words, the recording materials produced with the colour developers according to the invention surprisingly have a desirable high starting temperature.

The compound according to claim 1 has the formula (I),

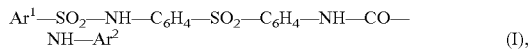
(I), wherein $Ar^1$ and $Ar^2$ are an unsubstituted or substituted phenyl group.

$Ar^1$ is preferably a phenyl group.

$Ar^2$ is preferably a phenyl group.

Especially preferably, $Ar^1$ is substituted with at least one $C_1$-$C_5$ alkyl group, an alkenyl group, an alkynyl group, a benzyl group, a formyl group, a CN group, a halogen group, an $NO_2$ group, an RO group, an R—CO— group, an $RO_2C$ group, an R—OCO group, an R—$SO_2O$ group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

$Ar^1$ is preferably substituted with at least one $C_1$-$C_5$ alkyl group, a halogen group, an RO group, an R—CO group or an $NO_2$ group, wherein R is a $C_1$-$C_5$ alkyl group.

$Ar^1$ is preferably substituted once.

Especially preferably, $Ar^2$ is substituted with at least one $C_1$-$C_5$ alkyl group, an alkenyl group, an alkynyl group, a benzyl group, a formyl group, a CN group, a halogen group, an $NO_2$ group, an RO group, an R—CO group, an $RO_2C$ group, an R—OCO group, an R—$SO_2O$ group, an R—O—$SO_2$ group, an R—$SO_2$—NH group, an R—NH—$SO_2$ group, an R—NH—CO group or an R—CO—NH group, wherein R is a $C_1$-$C_5$ alkyl group, an alkenyl group, an alkynyl group, a phenyl group, a tolyl group, or a benzyl group.

$Ar^2$ is preferably substituted with at least one $C_1$-$C_5$ alkyl group, a halogen group, an RO group, an R—CO group, an $RO_2C$ group or an $NO_2$ group, wherein R is a $C_1$-$C_5$ alkyl group.

$Ar^2$ is preferably substituted once.

$Ar^1$ and $Ar^2$ are substituted with at least one $C_1$-$C_5$ alkyl group, preferably in such a way that the $C_1$-$C_5$ alkyl group is a methyl group or butyl group, especially preferably a methyl group.

$Ar^1$ and $Ar^2$ are substituted with at least one halogen group preferably in such a way that the halogen group is a chloride group.

$Ar^1$ and $Ar^2$ are substituted with at least one RO group preferably in such a way that the R—CO group is a $CH_3O$ group.

$Ar^1$ and $Ar^2$ are substituted with at least one R—CO group preferably in such a way that the R—CO group is a $CH_3$—CO group.

In an especially preferred embodiment, both $Ar^1$ and $Ar^2$ are a phenyl group. Such compounds are relatively easy and inexpensive to produce and deliver good results in respect of the properties described below.

In a preferred embodiment, the $Ar^1$—$SO_2$—NH group and the $Ar^2$—NH—CO—NH group are arranged in the 4 and 4' position or in the 3 and 3' position to the —$C_6H_4$—$SO_2$—$C_6H_4$ group. The arrangement is especially in the 4 and 4' position, since such compounds are relatively easy to produce and show good properties.

Arrangement in the 4 and 4' position means that the $Ar^1$—SO—NH group and $Ar^2$—NH—CO—NH group are each arranged in the para-position to the —$C_4H_4$—$SO_2$—$C_6H_4$ group. Correspondingly, the 3 and 3' position means an arrangement in the meta position.

Especially preferred compounds of formula (I) are shown in Table 1 below:

TABLE 1

Preferred compounds of formula (I) with the stated meanings for the arrangement of the $Ar^1$—$SO_2$—NH and $Ar^2$—NH—CO—NH groups as well as the stated meaning of $Ar^1$ and $Ar^2$ (R as mentioned above).

| Arrangement of $Ar^1$—$SO_2$—NH— and $Ar^2$—NH—CO—NH— | $Ar^1$ | $Ar^2$ |
|---|---|---|
| 4,4' | phenyl | phenyl |
| 4,4' | $C_1$-$C_5$-alkyl-substituted phenyl | phenyl |
| 4,4' | tri-$C_1$-$C_5$-alkyl-substituted phenyl | phenyl |
| 4,4' | halogen-substituted phenyl | phenyl |
| 4,4' | RO-substituted phenyl | phenyl |
| 4,4' | R—CO-substituted phenyl | phenyl |
| 4,4' | nitro-substituted phenyl | phenyl |
| 4,4' | $C_1$-$C_5$-alkyl-substituted phenyl | $C_1$-$C_5$-alkyl-substituted phenyl |
| 4,4' | phenyl | $C_1$-$C_5$-alkyl-substituted phenyl |
| 4,4' | phenyl | halogen-substituted phenyl |
| 4,4' | phenyl | RO-substituted phenyl |
| 4,4' | phenyl | R—CO-substituted phenyl |
| 4,4' | phenyl | $RO_2C$-substituted phenyl |
| 4,4' | phenyl | nitro-substituted phenyl |
| 3,3' | phenyl | phenyl |

The compound of formula (I) according to the invention can be produced by methods known per se.

Reaction scheme 1 illustrates a possible synthesis pathway for the compound of formula (I) according to the invention using the example of compounds I to XVIII (see Table 2).

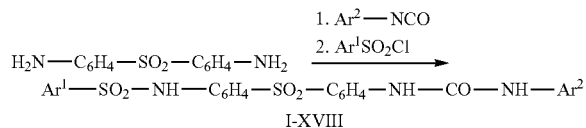

I-XVIII

Reaction scheme 1 (Ar$^1$, Ar$^2$: see Table 2;)

The preferred embodiments listed in conjunction with the compound of formula (I) also apply to the method for producing said compound.

As mentioned, the present invention also relates to a heat-sensitive recording material, comprising a carrier substrate and also a heat-sensitive, colour-forming layer containing at least one colour former and at least one phenol-free colour developer, the at least one phenol-free colour developer being the compound of the above-described formula (I).

The compound of formula (I) is preferably present in an amount of from about 3 to about 35% by weight, especially preferably in an amount of from about 10 to about 25% by weight, in relation to the total solids content of the heat-sensitive layer.

The selection of the carrier substrate is not critical. However, it is preferable to use paper, synthetic paper and/or a plastics film as the carrier substrate.

If necessary, there is at least one further intermediate layer between the carrier substrate and the heat-sensitive layer, with this intermediate layer having the task of improving the surface smoothness of the carrier substrate for the heat-sensitive layer and ensuring a thermal barrier between the carrier substrate and the heat-sensitive layer. Preferably, organic hollow sphere pigments and/or calcined kaolins are used in this intermediate layer. At least one protective layer and/or at least one layer promoting printability may also be present in the heat-sensitive recording material according to the invention, and these layers may be applied to the front or rear side of the substrate.

With regard to the choice of colour former, the present invention is also not subject to any major restrictions. However, the colour former is preferably a dye of the triphenylmethane, fluoran, azaphthalide and/or the fluorene type. A fluoran-type dye is a very especially preferred colour former, since its availability and balanced application properties make it possible to provide a recording material having an attractive price-performance ratio.

Especially preferred fluoran-type dyes are as follows:
3-diethylamino-6-methyl-7-anilinofluoran,
3-(N-ethyl-N-4-toludinamino)-6-methyl-7-anilinofluoran,
3-(N-ethyl-N-isoamylamino)-6-methyl-7-anilinofluoran,
3-diethylamino-6-methyl-7-(2,4-dimethylanilino)fluoran,
3-pyrrolidino-6-methyl-7-anilinofluoran,
3-(cyclohexyl-N-methylamino)-6-methyl-7-anilinofluoran,
3-diethylamino-7-(3-trifluoromethylanilino)fluoran,
3-N-n-dibutylamino-6-methyl-7-aminofluoran,
3-diethylamino-6-methyl-7-(3-methylanilino)fluoran,
3-N-n-dibutylamino-7-(2-chloroanilino)fluoran,
3-(N-ethyl-N-tetrahydrofurfurylamino)-6-methyl-7-anilinofluoran,
3-(N-methyl-N-propylamino)-6-methyl-7-anilinofluoran,
3-(N-ethyl-N-ethoxypropylamino)-6-methyl-7-anilinofluoran,
3-(N-ethyl-N-isobutylamino)-6-methyl-7-anilinofluoran and/or
3-dipentylamino-6-methyl-7-anilinofluoran.

The colour formers can be used as single substances, but also as arbitrary mixtures of two or more colour formers, provided that the desirable application properties of the recording materials according to the invention do not suffer as a result.

The colour former is preferably present in an amount of from about 5 to about 30% by weight, especially preferably in an amount of from about 8 to about 20% by weight, in relation to the total solids content of the heat-sensitive layer.

To control specific application properties, it may be advantageous if at least two of the compounds falling under the general formula (I) are present as colour developers in the heat-sensitive layer.

Likewise, one or more other (bis)phenolic or non-phenolic colour developer(s) may be present in the heat sensitive colour-forming layer in addition to the compound(s) of formula (I).

In addition to the at least one colour former and the at least one colour developer, the heat-sensitive colour-forming layer may contain one or more sensitising agents, also known as thermal solvents, which has the advantage that it is easier to control the thermal pressure sensitivity.

In general, crystalline substances with a melting point, between about 90 and about 150° C. are advantageously used as sensitising agents, and, in the molten state, dissolve the colour-forming components (colour former and colour developer) without disturbing the formation of the colour complex.

Preferably, the sensitising agent is a fatty acid amide, such as stearamide, behenamide or palmitamide, an ethylene-bis-fatty acid amide, such as N,N-ethylene-bis-stearic acid amide or N,N-ethylene-bis-oleic acid amide, a fatty acid alkanolamide, such as N-(hydroxymethyl)stearamide, N-hydroxymethylpalmitamide or hydroxyethylstearamide, a wax, such as polyethylene wax or montan wax, a carboxylic acid ester, such as dimethyl terephthalate, dibenzyl terephthalate, benzyl-4-benzyloxybenzoate, di-(4-methylbenzyl) oxalate, di-(4-chlorobenzyl)oxalate or di-(4-benzyl)oxalate, ketones such as acetylbiphenyl, an aromatic ether such as 1,2-diphenoxy-ethane, 1,2-di(3-methylphenoxy)ethane, 2-benzoyloxynaphthalene, 1,2-bis(phenoxymethyl)benzene or 1,4-diethoxynaphthalen, an aromatic sulfone, such as diphenylsulfone, and/or an aromatic sulfonamide, such as 4-toluenesulfonamide, benzenesulfonanilide or N-benzyl-4-toluenesulfonamide, or aromatic hydrocarbons, such as 4-benzylbiphenyl.

The sensitising agent is preferably present in an amount of from about 10 to about 40% by weight, especially preferably in an amount of from about 15 to about 25% by weight, in relation to the total solids content of the heat-sensitive layer.

In addition to the colour former, the phenol-free colour developer and, optionally, the sensitising agent, in a further preferred embodiment at least one stabiliser (antioxidant) is present in the heat-sensitive colour-forming layer.

The stabiliser is preferably constituted by sterically hindered phenols, especially preferably 1,1,3-tris-(2-methyl-4-hydroxy-5-cyclohexyl-phenyl)-butane, 1,1,3-tris-(2-methyl-4-hydroxy-5-tert-butylphenyl)-butane and/or 1,1-bis-(2-methyl-4-hydroxy-5-tert-butyl-phenyl)-butane.

Also urea-urethane compounds of general formula (II) (commercial product UU) or ethers derived from 4,4'-dihydroxydiphenylsulfone, such as 4-benzyloxy-4'-(2-methyl-glycidyloxy)-diphenylsulfone (trade name NTZ-95®, Nippon Soda Co. Ltd.), or oligomeric ethers of general formula (III) (trade name D90®, Nippon Soda Co. Ltd.) can be used as stabilisers in the recording material according to the invention.

hydroxides, silicas, precipitated and pyrogenic silicas (for example Aerodisp® types), diatomaceous earths, magnesium carbonates, talc, kaolin, but also organic pigments, such as hollow pigments with a styrene/acrylate copolymer wall or urea/formaldehyde condensation polymers. These can be used alone or in any mixture.

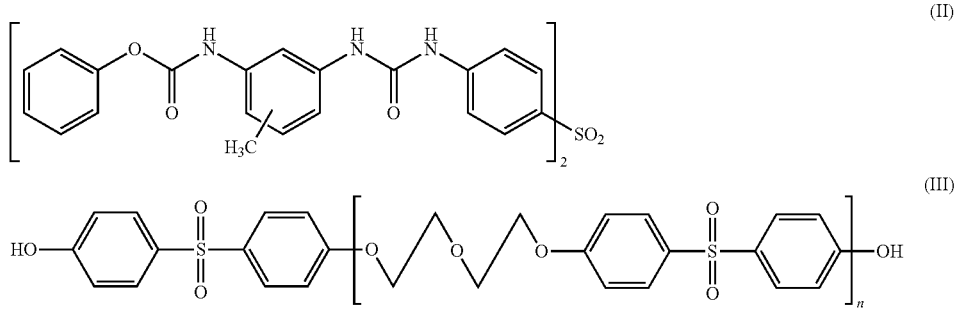

The urea-urethane compounds of general formula (II) are especially preferred.

The stabiliser is preferably present in an amount of about 0.2 to 0.5 parts by weight, in relation to 1 part by weight of the at least one phenol-free colour developer of the compound of formula (I).

In a further preferred embodiment, the heat-sensitive colour-forming layer contains at least one binder. These are preferably water-soluble starches, starch derivatives, starch-based biolatices of the EcoSphere® type, methyl cellulose, hydroxyethyl cellulose, carboxymethyl celluloses, partially or completely saponified polyvinyl alcohols, chemically modified polyvinyl alcohols, or styrene-maleic anhydride copolymers, styrene-butadiene copolymers, acrylamide-(meth)acrylate copolymers, acrylamide-acrylate-methacrylate terpolymers, polyacrylates, poly(meth)acrylic acid esters, acrylate-butadiene copolymers, polyvinyl acetates and/or acrylonitrile-butadiene copolymers.

In a further preferred embodiment, at least one release agent (anti-stick agent) or lubricant is present in the heat-sensitive colour-forming layer. These agents are preferably fatty acid metal salts, such as zinc stearate or calcium stearate, or behenate salts, synthetic waxes, for example in the form of fatty acid amides, such as stearic acid amide and behenic acid amide, fatty acid alkanol amides, such as stearic acid methylolamide, paraffin waxes of different melting points, ester waxes of different molecular weights, ethylene waxes, propylene waxes of different hardnesses and/or natural waxes, such as carnauba wax or montan wax.

The release agent is preferably present in an amount of from about 1 to about 10% by weight, especially preferably in an amount of from about 3 to about 6% by weight, in relation to the total solids content of the heat-sensitive layer.

In a further preferred embodiment, the heat-sensitive colour-forming layer contains pigments. One of the advantages of using these pigments is that they can fix on their surface the molten chemicals produced in the thermal printing process. Pigments can also be used to control the surface whiteness and opacity of the heat-sensitive colour-forming layer and its printability with conventional inks. Lastly, pigments have an "extender function", for example for the relatively expensive colouring functional chemicals.

Especially suitable pigments are inorganic pigments, both synthetic and natural, preferably clays, precipitated or natural calcium carbonates, aluminium oxides, aluminium The pigments are preferably present in an amount of from about 20 to about 50% by weight, especially preferably in an amount of from about 30 to about 40% by weight, in relation to the total solids content of the heat-sensitive layer.

To control the surface whiteness of the heat-sensitive recording material according to the invention, optical brighteners can be incorporated into the heat-sensitive colour-forming layer. These are preferably stilbenes.

In order to improve certain coating properties, it is preferable in individual cases to add further components, especially rheological auxiliaries such as thickeners and/or surfactants, to the stated components of the heat-sensitive recording material according to the invention.

The applied weight per unit area of the (dry) heat-sensitive layer is preferably about 1 to about 10 g/m$^2$, preferably about 3 to about 6 g/m$^2$.

In an especially preferred embodiment, the heat-sensitive recording material is one according to claim 10, in which a dye of the fluoran type is used as colour former and a sensitising agent, selected from the group consisting of fatty acid amides, aromatic sulfones and/or aromatic ethers, is additionally present. In this preferred embodiment it is also advantageous that about 1.5 to about 4 parts by weight of the phenol-free colour developer according to claim 1 are present in relation to 1 part by weight colour former.

The heat-sensitive recording material is especially preferably one according to claim 10, in which a dye of the fluoran type is used as colour former and at least one sensitising agent, preferably selected from the group consisting of fatty acid amides, aromatic sulfones and/or aromatic, ethers, especially preferably from aromatic ethers, at least one slip agent, which is preferably a fatty add metal salt, especially preferably zinc stearate or calcium stearate, at least one pigment, which is preferably an inorganic pigment, and at least one binder, which is preferably polyvinyl alcohol, are additionally present.

The preferred embodiments listed in conjunction with the compound of formula (I) also apply to the heat-sensitive recording material according to the invention.

The heat-sensitive recording material according to the invention can be obtained using known production methods. However, it is preferable to obtain the recording material according to the invention by a method in which an aqueous suspension containing the starting materials of the heat-sensitive colour-forming layer is applied to a carrier substrate and dried, the aqueous application suspension having a solids content of from about 20 to about 75% by weight, preferably of from about 30 to about 50% by weight, and is applied and dried by the curtain coating process at an operating speed of the coating plant of at least about 400 m/min.

This process is especially advantageous from an economic point of view.

If the solids content falls below the value of about 20% by weight, the economic efficiency is reduced because a large amount of water must be removed from the coating by gentle drying in a short time, which has a negative effect on the coating speed. If, on the other hand, the value of 75% by weight is exceeded, then this only leads to an increased technical effort to ensure the stability of the coating colour curtain during the coating process.

In the curtain coating process, a free-failing curtain of a coating dispersion is formed. By free fait, the coating dispersion, which is in the form of a thin film (curtain), is "poured" onto a substrate to apply the coating dispersion to the substrate. Document DE 10 196 052 T1 discloses the use of the curtain coating process in the production of information recording materials, also including, amongst other things, heat-sensitive recording materials, wherein multi-layer recording layers are realised by applying the curtain, which consists of several coating dispersion films, to substrates (speed maximum 200 m/min).

Setting the operating speed of the coating plant to at least about 400 m/min has both economic and technical advantages. Preferably, the operating speed is at least about 750 m/min, especially preferably at least about 1000 m/min, and very especially preferably at least about 1500 m/min. It was especially surprising that, even at the latter speed, the heat-sensitive recording material obtained is not affected in any way, and the operation runs optimally even at this high speed.

In a preferred embodiment of the method according to the invention, the aqueous deaerated coating suspension has a viscosity of about 150 to about 800 mPas (Brookfield, 100 rpm, 20° C.). If the viscosity falls below the value of about 150 mPas or exceeds the value of about 800 mPas, this leads to poor runnability of the coating mass at the coating unit. The viscosity of the aqueous deaerated coating suspension is especially preferably about 200 to about 500 mPas.

In a preferred embodiment, the surface tension of the aqueous application suspension can be adjusted to about 25 to about 60 mN/m, preferably to about 35 to about 50 mN/m (measured according to the static ring method according to Du Noüy, DIN 53914), in order to optimise the process.

The heat sensitive colour-forming layer can be formed on-line or in a separate coating process off-line. This also applies to any subsequently applied layers or intermediate layers.

It is advantageous if the dried heat-sensitive colour-forming layer is subjected to a smoothing measure. It is advantageous here to adjust the Bekk smoothness, measured according to ISO 5627:1995-03, to about 100 to about 1000 sec., preferably to about 250 to about 600 sec.

The surface roughness (PPS) according to ISO 8791-4:2008-05 is in the range of about 0.50 to about 2.50 μm, especially preferably in the range of 1.00 and 2.00 μm.

The preferred embodiments listed in conjunction with the compound of formula (I) also apply to the method according to the invention for producing the heat-sensitive recording material according to the invention.

The present invention also relates to a heat-sensitive recording material obtainable by the above-mentioned method.

The method described above is advantageous from an economic point of view and allows a high process performance of the coating plant even at a speed of more than 1500 m/min without any impairment of the process product, that is to say the heat-sensitive recording material according to the invention. The method can be carried out on-line and off-line, which results in a desirable flexibility.

The heat-sensitive recording material according to the invention is preferably phenol-free and well suited for POS (point-of-sale), label and/or ticket applications. It is also suitable for the production of parking tickets, travel tickets, admission tickets, lottery and betting tickets etc., which can be printed using the direct thermal process and require high resistance of the images recorded on them under long-term storage, even under harsh climatic conditions with regard to temperature and ambient humidity.

Surprisingly, it has been shown that, using the colour developers of formula (I) according to the invention it is possible to provide heat-sensitive recording materials which are characterised especially in that they do not lose practically any of their ability to produce high image densities, even after weeks of storage of the unprinted materials even in high ambient humidity and/or at high temperature. The heat-sensitive recording materials according to the invention therefore show a surprisingly long storage capability.

The Invention is explained in detail below on the basis of non-limiting examples.

EXAMPLES

Production of the Compounds of Formula (I) According to the Invention.

Non-phenolic colour developers from the prior art were used as comparative developers, specifically N-(2-(3-phenylureido)phenyl)benzene-sulfonamide (NKK1304, Nippon Soda) and a sulfonylurea, Pergafast 201®, BASF (PF201). Compounds I to XVIII (Table 2) were produced as follows (Protocol A):

A solution of 7.5 mmol of the corresponding isocyanate in 20 mL dichloromethane is added dropwise at 0° C. with stirring to a mixture of 7.5 mmol of aromatic diamine and 7.5 mmol pyridine in 80 mL dichloromethane. The reaction solution is stirred for 16 hours at room temperature. A solution of 7.5 mmol of the corresponding sulfonyl chloride in 15 ml dichloromethane is then added dropwise at 0° C. with stirring. The reaction mixture is refluxed and the progress of the reaction is monitored by means of HPLC. Once the reaction is complete, the product is filtered off, washed with dichloromethane, and dried in a vacuum. In some cases there is a further purification by recrystallisation from dichloromethane, ethanol, ethyl acetate or acetone and optionally a few drops of n-hexane.

The starting compounds are commercially obtainable.

Table 1 summarises the compounds of formula (I) produced for the first time.

TABLE 2

Composition of selected compounds of formula (I)

| | $-C_6H_4-SO_2-C_6H_4-$ | $Ar^1$ | $Ar^2$ |
|---|---|---|---|
| I | 4,4' | $C_6H_5$ | $C_6H_5$ |
| II | 4,4' | $4-CH_3-C_6H_4$ | $C_6H_5$ |

TABLE 2-continued

Composition of selected compounds of formula (I)

| | —$C_6H_4$—$SO_2$—$C_6H_4$— | $Ar^1$ | $Ar^2$ |
|---|---|---|---|
| III | 4,4' | 4-(tert-$C_4H_9$)—$C_6H_4$ | $C_6H_5$ |
| IV | 4,4' | 2,4,6-tri$CH_3$—$C_6H_2$ | $C_6H_5$ |
| V | 4,4' | 4-Cl—$C_6H_4$ | $C_6H_5$ |
| VI | 4,4' | 4-$CH_3O$—$C_6H_4$ | $C_6H_5$ |
| VII | 4,4' | 4-$CH_3CO$—$C_6H_4$ | $C_6H_5$ |
| VIII | 4,4' | 4-$NO_2$—$C_6H_4$ | $C_6H_5$ |
| IX | 4,4' | $C_6H_5$ | 2-$CH_3$—$C_6H_4$ |
| X | 4,4' | $C_6H_5$ | 3-$CH_3$—$C_6H_4$ |
| XI | 4,4' | $C_6H_5$ | 4-$CH_3$—$C_6H_4$ |
| XII | 4,4' | $C_6H_5$ | 4-Cl—$C_6H_4$ |
| XIII | 4,4' | $C_6H_5$ | 4-$CH_3O$—$C_6H_4$ |
| XIV | 4,4' | $C_6H_5$ | 4-$CH_3CO$—$C_6H_4$ |
| XV | 4,4' | $C_6H_5$ | 4-($CO_2C_2H_5$)—$C_6H_4$ |
| XVI | 4,4' | $C_6H_5$ | 4-$NO_2$—$C_6H_4$ |
| XVII | 4,4' | 4-$CH_3$—$C_6H_4$ | 4-$CH_3$—$C_6H_4$ |
| XVIII | 3,3' | $C_6H_5$ | $C_6H_5$ |

Analytical Data:

I, $C_{25}H_{21}N_3O_5S_2$, M=507.6, N-(4-((4'-(3-phenylureido)phenyl)sulfonyl)phenyl)benzenesulfonamide MS (ESI): m/z (%)=506.0 (100) [M–H]⁻.
¹H-NMR (500 MHz, DMSO-$d_6$): δ (ppm)=10.99 (1H, s), 9.16 (1H, s), 8.78 (1H, s), 7.85-7.84 (2H, m), 7.81-7.78 (4H, m), 7.65-7.63 (2H, m), 7.62-7.60 (1H, m), 7.57-7.55 (2H, m), 7.47-7.45 (2H, m), 7.31-7.27 (4H, m), 7.01-6.98 (1H, m).
¹³C-NMR (126 MHz, DMSO-$d_6$): δ (ppm)=152.01 (NHCONH), 144.45, 142.24, 139.18, 139.06, 136.10, 133.27, 133.25, 129.43, 128.74, 128.64, 128.48, 126.55, 122.28, 118.54, 118.49, 117.90.

II, $C_{26}H_{23}N_3O_5S_2$, M=521.6, N-(4-((4'-(3-phenylureido)phenyl)sulfonyl)phenyl)tosylamide MS (ESI): m/z (%)=522.1 (100) [M+H]₊.
¹H-NMR (500 MHz, DMSO-$d_6$): δ (ppm)=10.90 (1H, s), 9.15 (1H, s), 8.77 (1H, s), 7.79-7.77 (4H, m), 7.72-7.71 (2H, m), 7.64-7.62 (2H, m), 7.46-7.44 (2H, m), 7.35-7.34 (2H, m), 7.30-7.27 (4H, m), 7.01-6.98 (1H, m), 2.31 (3H, s).
¹³C-NMR (126 MHz, DMSO-$d_6$): δ (ppm)=151.99 (NHCONH), 144.42, 143.79, 142.34, 139.05, 136.28, 135.94, 133.26, 129.85, 128.73, 128.61, 128.46, 126.59, 122.27, 118.47, 118.39, 117.88, 20.88 ($CH_3$).

III, $C_{29}H_{29}N_3O_5S_2$, M=563.7, N-(4-((4'-(3-phenylureido)phenyl)sulfonyl)phenyl)-4-tert-butylbenzenesulfonamide MS (ESI): m/z (%)=564.2 (100) [M+H]₊.
¹H-NMR (500 MHz, DMSO-$d_6$): δ (ppm)=10.95 (1H, s), 9.15 (1H, s), 8.77 (1H, s), 7.80-7.76 (6H, m), 7.63-7.62 (2H, m), 7.58-7.56 (2H, m), 7.46-7.44 (2H, m), 7.31-7.27 (4H, m), 7.01-6.98 (1H, m), 1.23 (9H, s).
¹³C-NMR (126 MHz, DMSO-$d_6$): δ (ppm)=156.36 (NHCONH), 151.99, 144.42, 142.37, 139.05, 136.46, 135.86, 133.27, 128.73, 128.65, 128.44, 126.45, 126.28, 122.27, 118.46, 118.21, 117.86, 34.81, 30.58 ($CH_3$).

IV, $C_{28}H_{27}N_3O_5S_2$, M=549.7, N-(4-((4'-(3-phenylureido)phenyl)sulfonyl)phenyl)-2,4,6-trimethylbenzenesulfonamide MS (ESI): m/z (%)=550.1 (100) [M+H]₊.
¹H-NMR (500 MHz, DMSO-$d_6$): δ (ppm)=10.92 (1H, s), 9.25 (1H, s), 8.87 (1H, s), 7.78-7.75 (4H, m), 7.63-7.61 (2H, m), 7.46-7.44 (2H, m), 7.30-7.27 (2H, m), 7.12-7.10 (2H, m), 7.01 (2H, s), 7.01-6.97 (2H, m), 2.59 (6H, s), 2.20 (3H, s).
¹³C-NMR (126 MHz, DMSO-$d_6$): δ (ppm)=152.02 (NHCONH), 144.42, 142.57, 142.35, 139.08, 138.62, 135.32, 133.29, 133.27, 131.93, 128.72, 128.66, 128.44, 122.24, 118.42, 117.81, 117.20, 22.22 ($CH_3$), 20.30 ($CH_3$).

V, $C_{25}H_{20}ClN_3O_5S_2$, M=542.0, N-(4-((4'-(3-phenylureido)phenyl)sulfonyl)phenyl)-4-chlorobenzenesulfonamide MS (ESI): m/z (%)=540.0 (100) [M–H]⁻.
¹H-NMR (500 MHz, DMSO-$d_6$): δ (ppm)=11.05 (1H, s), 9.21 (1H, s), 8.82 (1H, s), 7.83-7.77 (6H, m), 7.64-7.62 (4H, m), 7.46-7.45 (2H, m), 7.30-7.27 (4H, m), 7.00-6.97 (1H, m).
¹³C-NMR (126 MHz, DMSO-$d_6$): δ (ppm)=152.01 (NHCONH), 144.49, 141.90, 139.07, 138.26, 137.98, 136.41, 133.13, 129.64, 128.74, 128.69, 128.50, 128.48, 122.27, 118.82, 118.45, 117.88.

VI, $C_{26}H_{23}N_3O_6S_2$, M=537.6, N-(4-((4'-(3-phenylureido)phenyl)sulfonyl)phenyl)-4-methoxybenzenesulfonamide MS (ESI): m/z (%)=536.1 (100) [M–H]⁻.
¹H-NMR (500 MHz, DMSO-$d_6$): δ (ppm)=10.84 (1H, s), 9.19 (1H, s), 8.81 (1H, s), 7.79-7.76 (6H, m), 7.64-7.62 (2H, m), 7.46-7.44 (2H, m), 7.30-7.27 (4H, m), 7.07-7.05 (2H, m), 7.01-6.98 (1H, m), 3.78 (3H, s).
¹³C-NMR (126 MHz, DMSO-$d_6$): δ (ppm)=162.72, 152.01 (NHCONH), 144.44, 142.44, 139.07, 135.83, 133.27, 130.65, 128.85, 128.75, 128.62, 128.46, 122.28, 118.46, 118.29, 117.87, 114.59, 55.60 ($OCH_3$).

VII, $C_{27}H_{23}N_3O_6S_2$, M=549.6, N-(4-((4'-(3-phenylureido)phenyl)sulfonyl)phenyl)-4-acetylbenzenesulfonamide MS (ESI): m/z (%)=550.1 (100) [M+H]₊.
¹H-NMR (500 MHz, DMSO-$d_6$): δ (ppm)=11.13 (1H, s), 9.14 (1H, s), 8.76 (1H, s), 8.09-8.08 (2H, m), 7.97-7.95 (2H, m), 7.81-7.79 (2H, m), 7.78-7.77 (2H, m), 7.63-7.61 (2H, m), 7.45-7.44 (2H, m), 7.31-7.30 (2H, m), 7.30-7.27 (2H, m), 7.01-6.98 (1H, m), 2.57 (3H, s).
¹³C-NMR (126 MHz, DMSO-$d_6$): δ (ppm)=196.95 ($COCH_3$), 151.96 (NHCONH), 144.45, 142.64, 141.85, 140.06, 139.02, 136.41, 133.11, 129.13, 128.70, 128.67, 128.47, 126.90, 122.26, 118.74, 118.46, 117.87, 26.84 ($CH_3$).

VIII, $C_{25}H_{20}N_4O_7S_2$, M=552.6, N-(4-((4'-(3-phenylureido)phenyl)sulfonyl)phenyl)-4-nitrobenzenesulfonamide MS (ESI): m/z (%)=551.0 (100) [M–H]⁻.
¹H-NMR (500 MHz, DMSO-$d_6$): δ (ppm)=11.30 (1H, s), 9.24 (1H, s), 8.85 (1H, s), 8.37-8.36 (2H, m), 8.09-8.07 (2H, m), 7.83-7.81 (2H, m), 7.79-7.77 (2H, m), 7.64-7.62 (2H, m), 7.46-7.44 (2H, m), 7.33-7.31 (2H, m), 7.30-7.26 (2H, m), 7.00-6.97 (1H, m).
$^{13}$C-NMR (126 MHz, DMSO-d$_6$): δ (ppm)=152.02 (NHCONH), 150.05, 144.55, 144.43, 141.49, 139.07, 136.81, 133.01, 128.75, 128.73, 128.55, 128.18, 124.82, 122.26, 119.09, 118.44, 117.87.

IX, $C_{26}H_{23}N_3O_5S_2$, M=521.6, N-(4-((4'-(3-(2-tolyl)ureido)phenyl)sulfonyl)phenyl)benzenesulfonamide MS (ESI): m/z (%)=520.1 (100) [M−H]$^-$.
$^1$H-NMR (500 MHz, DMSO-d$_6$): δ (ppm)=10.97 (1H, s), 9.46 (1H, s), 8.04 (1H, s), 7.85-7.83 (2H, m), 7.80-7.76 (5H, m), 7.65-7.60 (3H, m), 7.58-7.55 (2H, m), 7.31-7.28 (2H, m), 7.19-7.13 (2H, m), 6.98 (1H, ddd, J=8.5, 7.4, 1.1 Hz), 2.24 (3H, s).
$^{13}$C-NMR (126 MHz, DMSO-d$_6$): δ (ppm)=152.16 (NHCONH), 144.56, 142.19, 139.16, 136.71, 136.11, 133.25, 133.11, 130.14, 129.40, 128.59, 128.49, 128.19, 126.51, 126.07, 123.24, 121.54, 118.52, 117.71, 17.68 (CH$_3$).

X, $C_{26}H_{23}N_3O_5S_2$, M=521.6, N-(4-((4'-(3-(3-tolyl)ureido)phenyl)sulfonyl)phenyl)benzenesulfonamide MS (ESI): m/z (%)=520.1 (100) [M−H]$^-$.
$^1$H-NMR (500 MHz, DMSO-d$_6$): δ (ppm)=10.97 (1H, s), 9.14 (1H, s), 8.70 (1H, s), 7.85-7.83 (2H, m), 7.80-7.76 (4H, m), 7.64-7.60 (3H, m), 7.58-7.55 (2H, m), 7.30-7.28 (3H, m), 7.24-7.22 (1H, m), 7.18-7.15 (1H, m), 6.82-6.81 (1H, m), 2.24 (3H, s).
$^{13}$C-NMR (126 MHz, DMSO-d$_6$): δ (ppm)=151.96 (NHCONH), 144.45, 142.19, 139.17, 138.95, 137.93, 136.10, 133.25, 133.18, 129.40, 128.60, 128.54, 128.44, 126.51, 123.01, 118.97, 118.52, 117.83, 115.65, 21.08 (CH$_3$).

XI, $C_{26}H_{23}N_3O_5S_2$, M=521.6, N-(4-((4'-(3-(4-tolyl)ureido)phenyl)sulfonyl)phenyl)benzenesulfonamide MS (ESI): m/z (%)=520.1 (100) [M−H]$^-$.
$^1$H-NMR (500 MHz, DMSO-d$_6$): δ (ppm)=10.98 (1H, s), 9.17 (1H, s), 8.72 (1H, s), 7.84-7.83 (2H, m), 7.79-7.78 (2H, m), 7.77-7.75 (2H, m), 7.64-7.61 (3H, m), 7.58-7.55 (2H, m), 7.34-7.33 (2H, m), 7.29-7.28 (2H, m), 7.10-7.08 (2H, m), 2.23 (3H, s).
$^{13}$C-NMR (126 MHz, DMSO-d$_6$): δ (ppm)=152.02 (NHCONH), 144.54, 142.19, 139.16, 136.47, 136.12, 133.27, 133.07, 131.17, 129.42, 129.11, 128.60, 128.44, 126.52, 118.55, 118.52, 117.78, 20.25 (CH$_3$).

XII, $C_{25}H_{20}ClN_3O_5S_2$, M=542.0, N-(4-((4'-(3-(4-chlorophenyl)ureido)phenyl)sulfonyl)phenyl)benzenesulfonamide MS (ESI): m/z (%)=542.0 (100) [M+H]$_+$.
$^1$H-NMR (500 MHz, DMSO-d$_6$): δ (ppm)=10.97 (1H, s), 9.19 (1H, s), 8.92 (1H, s), 7.84-7.82 (2H, m), 7.79-7.78 (2H, m), 7.78-7.76 (2H, m), 7.64-7.61 (3H, m), 7.58-7.55 (2H, m), 7.49-7.47 (2H, m), 7.35-7.32 (2H, m), 7.30-7.27 (2H, m).
$^{13}$C-NMR (126 MHz, DMSO-d$_6$): δ (ppm)=151.92 (NHCONH), 144.24, 142.21, 139.15, 138.07, 136.03, 133.41, 133.27, 129.42, 128.63, 128.57, 128.44, 126.52, 125.86, 120.01, 118.51, 118.00.

XIII, $C_{26}H_{23}N_3O_6S_2$, M=537.6, N-(4-((4'-(3-(4-methoxyphenyl)ureido)phenyl)sulfonyl)phenyl)benzenesulfonamide MS (ESI): m/z (%)—538.0 (100) [M+H]$_+$.
$^1$H-NMR (500 MHz, DMSO-d$_6$): δ (ppm)=10.97 (1H, s), 9.08 (1H, s), 8.58 (1H, s), 7.85-7.82 (2H, m), 7.80-7.78 (2H, m), 7.77-7.75 (2H, m), 7.64-7.60 (3H, m), 7.58-7.54 (2H, m), 7.37-7.34 (2H, m), 7.30-7.27 (2H, m), 6.89-5.86 (2H, m), 3.71 (3H, s).
$^{13}$C-NMR (126 MHz, DMSO-d$_6$): δ (ppm)=154.81, 152.16 (NHCONH), 144.63, 142.21, 139.17, 136.13, 133.27, 132.99, 132.02, 129.43, 128.60, 128.44, 126.53, 120.37, 118.52, 117.76, 113.98, 55.13 (OCH$_3$).

XIV, $C_{27}H_{23}N_3O_6S_2$, M=549.6, N-(4-((4'-(3-(4-acetylphenyl)ureido)phenyl)sulfonyl)phenyl)benzenesulfonamide MS (ESI): m/z (%)—550.1 (100) [M+H]+.
$^1$H-NMR (500 MHz, DMSO-d$_6$): δ (ppm)=10.98 (1H, s), 9.28 (1H, s), 9.20 (1H, s), 7.92-7.90 (2H, m), 7.84-7.83 (2H, m), 7.80-7.78 (4H, m), 7.65-7.55 (7H, m), 7.30-7.27 (2H, m), 2.51 (3H, s).
$^{13}$C-NMR (126 MHz, DMSO-d$_6$): δ (ppm)=196.20 (COCH$_3$), 151.73 (NHCONH), 144.02, 143.66, 142.25, 139.16, 135.99, 133.69, 133.29, 130.86, 129.53, 129.43, 128.66, 128.47, 126.53, 118.52, 118.17, 117.43, 26.24 (CH$_3$).

XV, $C_{28}H_{25}N_3O_7S_2$, M=579.6, ethyl 4-(3-(4-((4'-(phenylsulfonamido)phenyl)sulfonyl)phenyl)ureido)benzoate MS (ESI): m/z (%)—580.1 (100) [M+H]$_+$.
$^1$H-NMR (500 MHz, DMSO-d$_6$): δ (ppm)=10.98 (1H, s), 9.25 (1H, s), 9.18 (1H, s), 7.91-7.89 (2H, m), 7.85-7.83 (2H, m), 7.81-7.80 (2H, m), 7.79-7.78 (2H, m), 7.66-7.54 (7H, m), 7.30-7.27 (2H, m), 3.45 (2H, q, J=6.9 Hz), 1.06 (3H, t, J=7.0 Hz).
$^{13}$C-NMR (126 MHz, DMSO-d$_6$): δ (ppm)=165.29 (COO), 151.73 (NHCONH), 144.02, 143.65, 142.29, 139.18, 135.97, 133.70, 133.27, 130.26, 129.42, 128.66, 128.47, 126.54, 123.26, 118.52, 118.16, 117.56, 60.23 (CH$_2$), 14.14 (CH$_3$).

XVI, $C_{25}H_{20}N_4O_7S_2$, M=552.6, N-(4-((4'-(3-(4-nitrophenyl)ureido)phenyl)sulfonyl)phenyl)benzenesulfonamide MS (ESI): m/z (%)—553.0 (100) [M+H]$^+$.
$^1$H-NMR (500 MHz, DMSO-d$_6$): δ (ppm)=10.99 (1H, s), 9.52 (1H, s), 9.38 (1H, s), 8.20-8.18 (2H, m), 7.85-7.83 (2H, m), 7.81-7.80 (2H, m), 7.80-7.79 (2H, m), 7.70-7.68 (2H, m), 7.66-7.64 (2H, m), 7.62-7.60 (1H, m), 7.57-7.54 (2H, m), 7.30-7.28 (2H, m).
$^{13}$C-NMR (126 MHz, DMSO-d$_6$): δ (ppm)=151.61 (NHCONH), 145.71, 143.76, 142.30, 141.40, 139.16, 135.92, 134.03, 133.30, 129.45, 128.71, 128.49, 126.55, 125.01, 118.53, 118.40, 117.80.

XVII, $C_{27}H_{25}N_3O_5S_2$, M=535.6, N-(4-((4'-(3-(4-tolyl)ureido)phenyl)sulfonyl)phenyl)tosylamide MS (ESI): m/z (%)=534.1 (100) [M−H]$^-$.
$^1$H-NMR (500 MHz, DMSO-d$_6$): δ (ppm)=10.88 (1H, s), 9.10 (1H, s), 8.66 (1H, s), 7.78-7.77 (2H, m), 7.77-7.75 (2H, m), 7.72-7.70 (2H, m), 7.63-7.61 (2H, m), 7.35-7.34 (2H, m), 7.34-7.32 (2H, m), 7.28-7.26 (2H, m), 7.10-7.08 (2H, m), 2.31 (3H, s), 2.24 (3H, s).

$^{13}$C-NMR (126 MHz, DMSO-d$_6$): δ (ppm)=151.99 (NHCONH), 144.49, 143.71, 142.41, 136.43, 136.34, 135.88, 133.14, 131.16, 129.80, 129.08, 128.55, 128.40, 126.55, 118.56, 118.39, 117.77, 20.84 (CH$_3$), 20.22 (CH$_3$).

XVIII, $C_{25}H_{21}N_3O_5S_2$, M=507.6, N-(3-((3'-(3-phenylureido)phenyl)sulfonyl)phenyl)benzenesulfonamide MS (ESI): m/z (%)—508.0 (100) [M+H]$_+$.

$^1$H-NMR (500 MHz, DMSO-d$_6$): δ (ppm)=10.75 (1H, bs), 9.10 (1H, bs), 8.73 (1H, s), 8.18-8.17 (1H, m), 7.73-7.71 (2H, m), 7.67-7.66 (1H, m), 7.61-7.55 (3H, m), 7.51-7.47 (5H, m), 7.38-7.33 (2H, m), 7.31-7.28 (2H, m), 7.01-6.98 (2H, m).

$^{13}$C-NMR (126 MHz, DMSO-d$_6$): δ (ppm)=152.32 (NHCONH), 141.97, 141.05, 140.90, 139.16, 138.87, 138.74, 133.10, 130.77, 130.18, 129.22, 128.70, 126.52, 126.49, 124.21, 122.85, 122.20, 120.13, 118.56, 117.20, 115.95.

An aqueous coating suspension was applied to one side of a 63 g/m$^2$ synthetic base paper (Yupo® FP680) using a doctor bar on a laboratory scale to form the heat-sensitive colour-forming layer of a heat-sensitive recording paper. After drying, a thermal recording sheet was obtained. The application rate of the heat-sensitive colour-forming layer was between 3.8 and 4.2 g/m$^2$.

On the basis of the above information, a heat-sensitive recording material or thermal paper was produced, with the following formulations of aqueous application suspensions being used to form a composite structure on a carrier substrate, and then the other layers, especially a protective layer, being formed in the usual manner, which will not be discussed separately here.

Production of the Dispersions (in Each Case for 1 Part by Weight) for the Application Suspensions The aqueous dispersion A (colour former dispersion) is produced by grinding 20 parts by weight of 3-N-n-dibutylamino-6-methyl-7-anilinofluoran (ODB-2) with 33 parts by weight of a 15% aqueous solution of Ghosenex™ L-3266 (sulfonated polyvinyl alcohol, Nippon Ghosei) in a bead mill.

The aqueous dispersion B (colour developer dispersion) is produced by grinding 40 parts by weight of the colour developer together with 66 parts by weight of a 15% aqueous solution of Ghosenex™ L-3266 in a bead mill.

The aqueous dispersion C (sensitising agent dispersion) is produced by grinding 40 parts by weight of 1,2-di(3-methylphenoxy)ethane with 33 parts by weight of a 15% aqueous solution of Ghosenex™ L-3266 in a bead mill.

All dispersions produced by grinding have an average particle size $D_{(4,3)}$ of 0.80 to 1.20 μm. The particle size distribution of the dispersions was measured by laser diffraction using a Coulter LS230 instrument from Beckman Coulter.

Dispersion D (lubricant dispersion) is a 20% zinc stearate dispersion consisting of 9 parts by weight of Zn-stearate, 1 part by weight of Ghosenex™ L-3266, and 40 parts by weight of water.

Pigment P is a 72% coating kaolin suspension (Lustra® S, BASF).

The binder consists of a 10% aqueous polyvinyl alcohol solution (Mowiol 28-99, Kuraray Europe).

The heat-sensitive application suspension is produced by mixing, with stirring, 1 part of A, 1 part of B, 1 part of C, 56 parts of D, 146 parts of pigment P and 138 parts of binder solution (all parts by weight), taking into account the order of introduction B, D, C, P, A, binder, and bringing the mixture to a solids content of about 25% with water.

The heat-sensitive coating suspensions obtained in this way were used to produce composite structures consisting of paper carrier and thermal reaction layer.

The thermal recording materials were evaluated as described below (see Tables 3, 4 and 5).

(1) Dynamic Colour Density:

The papers (6 cm wide strips) were thermally printed with a chessboard pattern with 10 energy levels using an Atlantek 200 test printer (Atlantek, USA) with a Kyocera print bar of 200 dpi and 560 ohms at an applied voltage of 20.6 V and a maximum pulse width of 0.8 ms. The image density (optical density, o.d.) was measured with a SpectroEye densitometer from X-Rite at an energy level of 0.45 mJ/dot. The measurement uncertainty of the o.d. values is estimated at ≤2%.

(2) Static Colour Density (Starting Temperature):

The recording sheet was pressed against a series of thermostatically controlled metallic stamps heated to different temperatures with a contact pressure of 0.2 kg/cm$^2$ and a contact time of 5 seconds (thermal tester TP 3000QM, Maschinenfabrik Hans Rychiger A G, Steffisburg, Switzerland). The image density (opt. density) of the images thus produced was measured with a SpectroEye densitometer from X-Rite.

The static starting point is, by definition, the lowest temperature at which an optical density of 0.2 is achieved. The accuracy of the measuring method is ≤±0.5° C.

(3) Resistance Test of the Printed Image a) Resistance Test of the Printed Image Under Artificial Ageing Conditions:

A sample of the thermal recording paper recorded dynamically in accordance with the method from 1) was stored for 7 days under each of the following conditions: i) 50° C. (dry ageing), ii) 40° C., 85% relative humidity (damp ageing) and iii) under artificial light from fluorescent tubes, illumination level 16000 Lux (light ageing).

Once the test time had passed, the image density was measured at an applied energy of 0.45 mJ/dot and was set in relation to the corresponding image density values prior to the artificial ageing in accordance with the formula (Eq. 1).

$$\% \text{ remaining image density} = \left(\frac{\text{image density after test}}{\text{image density before test}}\right) * 100 \quad \text{(Eq. 1)}$$

The spread of the % values calculated according to (Eq. 1) is ≤±2 percentage points.

b) Resistance to Plasticiser:

A plasticiser-containing plastic wrap (PVC film with 20 to 25% dioctyladipate) was brought into contact with the sample of thermal recording paper recorded dynamically in accordance with the method from (1), avoiding folds and inclusions of air, wound into a roll, and stored for 16 hours, A second sample was stored at 40° C. at room temperature (20 to 22° C.). Once the film had been removed, the image density (o.d.) was measured and set in relation with the corresponding image density values prior to the plasticiser influence in accordance with the formula (Eq. 1).

c) Resistance to Adhesive:

A strip of transparent tesa self-adhesive tape (tesafilm® crystal-clear, #57315) and, separately, a strip of tesa packaging adhesive tape (#04204) were glued to the sample of thermal recording paper dynamically recorded in accordance with the method from (1), avoiding folds and inclusions of air. Following storage at room temperature (20 to 22° C.), the Image density (o.d.) was measured after 24 hours and after 7 days—through the adhesive tape in question—and was set in relation to the image density values, determined in a similar way, of the freshly glued sample in accordance with the formula (Eq. 1).

(4) Shelf Life of the Imprinted Thermal Paper:

A sheet of recording paper was cut into three identical strips. One strip was dynamically recorded according to the process from (1) and the image density was determined. The other two strips were stored in the unprinted (white) state for 4 weeks in a climate of a) 40° C. and 85% relative humidity (r. h.) and b) 60° C. and 50% relative humidity (r. h.).

After conditioning the papers at room temperature, they were dynamically printed in accordance with the method from (1) and the image density was determined using a densitometer at an applied energy of 0.45 mJ/dot. The remaining writing performance (%) of the stored samples in relation to the fresh (not aged) samples was calculated according to equation (Eq. 1).

Tables 3 to 5 summarise the evaluation of the recording materials produced.

TABLE 3

Image density, starting temperature and artificial ageing

| Colour developer | o.d. (0.45 mJ/dot) | Starting point (° C.) | Artificial ageing* | | |
|---|---|---|---|---|---|
| | | | dry | damp | light |
| I | 1.27 | 91 | 99 | 100 | 78 |
| II | 1.24 | 97 | 98 | 100 | 73 |
| IV | 1.15 | 96 | 99 | 99 | 69 |
| V | 1.22 | 92 | 97 | 99 | 74 |
| VI | 1.22 | 97 | 100 | 98 | 75 |
| VII | 1.20 | 104 | 99 | 98 | 74 |
| VIII | 1.23 | 96 | 98 | 99 | 74 |
| X | 1.22 | 80 | 99 | 98 | 81 |
| XI | 1.19 | 81 | 98 | 100 | 77 |
| XII | 1.22 | 90 | 98 | 98 | 77 |
| XIII | 1.23 | 96 | 100 | 98 | 88 |
| XIV | 1.17 | 85 | 99 | 98 | 74 |
| XV | 1.20 | 81 | 98 | 99 | 78 |
| XVI | 1.28 | 84 | 98 | 97 | 83 |
| Comparative example NKK1304 | 1.21 | 87 | 99 | 99 | 68 |
| Comparative example PF201 | 1.15 | 81 | 99 | 98 | 66 |

*Percentage of remaining image density in accordance with Eq. 1

TABLE 4

Resistance of the printed image

| Colour developer | Tesa adhesive tape* | | | | Plasticiser film* | |
|---|---|---|---|---|---|---|
| | 24 h | | 7 days | | 16 h | |
| | #57315 | #04204 | #57315 | #04204 | R.T. | 40° C. |
| I | 75 | 49 | 50 | 30 | 96 | 84 |
| II | 81 | 57 | 45 | 30 | 98 | 71 |
| IV | 84 | 64 | 54 | 32 | 99 | 70 |

TABLE 4-continued

Resistance of the printed image

| Colour developer | Tesa adhesive tape* | | | | Plasticiser film* | |
|---|---|---|---|---|---|---|
| | 24 h | | 7 days | | 16 h | |
| | #57315 | #04204 | #57315 | #04204 | R.T. | 40° C. |
| V | 73 | 45 | 38 | 22 | 98 | 91 |
| VI | 76 | 61 | 48 | 29 | 96 | 88 |
| VII | 86 | 78 | 69 | 52 | 99 | 84 |
| VIII | 81 | 64 | 56 | 33 | 98 | 84 |
| X | 83 | 68 | 66 | 48 | 98 | 87 |
| XI | 84 | 65 | 64 | 40 | 96 | 92 |
| XII | 80 | 65 | 55 | 36 | 97 | 88 |
| XIII | 85 | 74 | 63 | 47 | 98 | 92 |
| XIV | 89 | 89 | 76 | 72 | 94 | 96 |
| XV | 82 | 73 | 60 | 50 | 97 | 93 |
| XVI | 88 | 82 | 75 | 65 | 98 | 84 |
| Comparative example NKK1304 | 50 | 27 | 15 | 13 | 83 | 21 |
| Comparative example PF201 | 63 | 38 | 28 | 14 | 93 | 69 |

*Percentage of remaining image density in accordance with Eq. 1

TABLE 5

Writing performance after storage

| Developer | o.d. prior to storage | 4 weeks 40° C./ 85% r.h. | | 4 weeks 60° C./ 50% r.h. | |
|---|---|---|---|---|---|
| | | o.d. after storage | remaining o.d. (%) | o.d. after storage | remaining o.d. (%) |
| I | 1.27 | 1.27 | 100 | 1.05 | 83 |
| II | 1.24 | 1.24 | 100 | 1.02 | 82 |
| IV | 1.15 | 1.15 | 100 | 0.77 | 67 |
| V | 1.22 | 1.22 | 100 | 0.98 | 80 |
| VI | 1.22 | 1.22 | 100 | 0.88 | 72 |
| VII | 1.20 | 1.19 | 99 | 1.04 | 87 |
| VIII | 1.23 | 1.23 | 100 | 0.82 | 67 |
| X | 1.22 | 1.21 | 99 | 1.02 | 84 |
| XI | 1.19 | 1.19 | 100 | 1.04 | 87 |
| XII | 1.22 | 1.22 | 100 | 1.05 | 86 |
| XIII | 1.23 | 1.22 | 99 | 1.09 | 89 |
| XIV | 1.17 | 1.17 | 100 | 1.03 | 88 |
| XV | 1.20 | 1.20 | 100 | 1.10 | 92 |
| XVI | 1.28 | 1.28 | 100 | 1.05 | 82 |
| Comparative example NKK1304 | 1.21 | 1.21 | 100 | 1.09 | 90 |
| Comparative example PF201 | 1.15 | 1.13 | 98 | 0.70 | 61 |

*Percentage of remaining image density in accordance with Eq. 1

It can be deduced from the above examples that the heat-sensitive recording material of the present invention shows the following advantageous properties especially:

(1) The recorded image of the heat-sensitive recording materials based on the colour developers according to the Invention has print densities (optical densities) which are better than/comparable to those of the comparative examples with known colour developers (Table 3).

(2) The temperature from which a visually perceptible greying of the recording materials according to the invention occurs (static starting point) is higher than that of the comparative examples with known colour developers and largely meets the requirements for marketable heat-sensitive recording materials (Table 3).

(3) The heat-sensitive recording materials subjected to the ageing test reveal a high image stability, better than or comparable to that of the comparative examples with known colour developers (Table 3).

(4) the print image is hardly faded or only slightly faded following the effect of hydrophobic agents (adhesives, plasticiser). The image resistance is better than or comparable to that of heat-sensitive recording materials with known non-phenolic colour developers (Table 4).

(5) Printing of the heat-sensitive recording materials stored for several weeks under extreme conditions results in image densities that are practically identical to those of unstored (fresh) heat-sensitive recording materials (Table 5).

(6) A heat-sensitive recording material that is considered to be high-quality in all key respects of its application can be obtained with the colour developers according to the invention, No recording material based on known colour developers has a comparably good/balanced performance profile over ail tested properties.

The invention claimed is:

1. A heat-sensitive recording material comprising a carrier substrate and a heat-sensitive colour-forming layer, which contains at least one colour former and at least one phenol-free colour developer, wherein the at least one phenol-free colour developer is a compound of formula (I), $Ar^1-SO_2-NH-C_6H_4-SO_2-C_6H_4-NH-CO-NH-Ar^2$ (I), wherein $Ar^1$ and $Ar^2$ are an unsubstituted or substituted phenyl group; and wherein the $Ar^1-SO_2-NH$ group and the $Ar^2-NH-CO-NH$ group are arranged in the 4 and 4' position or in the 3 and 3' position, to the $-C_6H_4-SO_2-C_6H_4$ group.

2. The heat-sensitive recording material according to claim 1, wherein the $Ar^1$ is a phenyl group.

3. The heat-sensitive recording material according to claim 1, wherein the $Ar^2$ is a phenyl group.

4. The heat-sensitive recording material according to claim 1, wherein the $Ar^1$ is substituted with at least one $C_1$-$C_5$ alkyl group, an alkenyl group, an alkynyl group, a benzyl group, a formyl group, a CN group, a halogen group, an $NO_2$ group, an RO group, an R—CO group, an $RO_2C$ group, an R—OCO group, an R—$SO_2$O group, an R—O—$SO_2$ group, an R—$SO_2$—NH group, an R—NH—$SO_2$ group, an R—NH—CO group or an R—CO—NH group, wherein the R is a $C_1$-$C_5$ alkyl group, an alkenyl group, an alkynyl group, a phenyl group, a tolyl group, or a benzyl group.

5. The heat-sensitive recording material according to claim 1, wherein the $Ar^1$ is a phenyl group substituted once.

6. The heat-sensitive recording material according to claim 1, wherein the $Ar^2$ is substituted with at least one $C_1$-$C_5$ alkyl group, an alkenyl group, an alkynyl group, a benzyl group, a formyl group, a CN group, a halogen group, an $NO_2$ group, an RO group, an ROC group, an $RO_2C$ group, an R—OCO group, an R—$SO_2$O group, an R—O—$SO_2$ group, an R—$SO_2$—NH group, an R—NH—$SO_2$ group, an R—NH—CO group or an R—CO—NH group, wherein the R is a $C_1$-$C_5$ alkyl group, an alkenyl group, an alkynyl group, a phenyl group, a tolyl group, or a benzyl group.

7. The heat-sensitive recording material according to claim 1, wherein the $Ar^2$ is a phenyl group substituted once.

8. The heat-sensitive recording material according to claim 1, wherein the $Ar^1$ is a phenyl group, and wherein the $Ar^2$ is a phenyl group.

9. The heat-sensitive recording material according to claim 1, wherein the colour developer is present in an amount of about 3 to about 35% by weight, in relation to a total solids content of the heat-sensitive layer.

10. The heat-sensitive recording material according to claim 1, wherein the at least one colour former is a triphenylmethane, a fluoran, an azaphthalide and/or a fluorene.

11. The heat-sensitive recording material according to claim 1, wherein one or more non-phenolic colour developers are present in addition to the at least one phenol-free colour developer.

12. A method for producing a heat-sensitive recording material according to claim 1, wherein an aqueous suspension comprising starting materials of the heat-sensitive colour-forming layer is applied to a carrier substrate and dried, wherein the aqueous application suspension has a solids content of an amount of about 20 to about 75% by weight, and is applied and dried by a curtain coating process at an operating speed of a coating plant of at least about 400 m/min.

13. The method for producing a heat-sensitive recording material according to claim 12, wherein the aqueous suspension has a solids content of an amount of about 30 to about 50% by weight.

14. The method for producing a heat-sensitive recording material according to claim 12, wherein an aqueous suspension containing the starting materials of the heat-sensitive colour-forming layer is applied to a carrier substrate and dried by the curtain coating process at an operating speed of the coating plant of at least about 1000 m/min.

15. The method for producing a heat-sensitive recording material according to claim 12, wherein an aqueous suspension containing the starting materials of the heat-sensitive colour-forming layer is applied to a carrier substrate and dried by the curtain coating process at an operating speed of the coating plant of at least about 1500 m/min.

16. The heat-sensitive recording material according to claim 1, wherein the colour developer is present in an amount of about 10 to about 25% by weight, in relation to the a total solids content of the heat-sensitive layer.

17. The heat-sensitive recording material according to claim 1, wherein the at least one colour former is a fluoran.

* * * * *